(12) United States Patent
Williams et al.

(10) Patent No.: US 10,751,049 B2
(45) Date of Patent: Aug. 25, 2020

(54) LOADING UNIT ATTACHMENT BAND FOR SURGICAL STAPLING INSTRUMENT

(71) Applicant: Covidien LP, Mansfield, MA (US)

(72) Inventors: Justin Williams, Southbury, CT (US); Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 154 days.

(21) Appl. No.: 16/136,987

(22) Filed: Sep. 20, 2018

(65) Prior Publication Data

US 2019/0015097 A1    Jan. 17, 2019

Related U.S. Application Data

(62) Division of application No. 14/804,814, filed on Jul. 21, 2015, now Pat. No. 10,085,744.

(60) Provisional application No. 62/088,729, filed on Dec. 8, 2014.

(51) Int. Cl.
*A61B 17/115* (2006.01)
*A61B 17/068* (2006.01)
*A61B 17/00* (2006.01)

(52) U.S. Cl.
CPC ........ *A61B 17/068* (2013.01); *A61B 17/1155* (2013.01); *A61B 2017/0046* (2013.01); *A61B 2017/00473* (2013.01); *A61B 2017/00477* (2013.01); *A61B 2017/00526* (2013.01)

(58) Field of Classification Search
CPC .............. A61B 17/068; A61B 17/1155; A61B 2017/00473; A61B 2017/0046; A61B 2017/00526; A61B 2017/00477

USPC ...................... 227/175.1–182.1; 606/142–143
See application file for complete search history.

(56) References Cited

U.S. PATENT DOCUMENTS

| | | | |
|---|---|---|---|
| 2,110,397 A | 3/1938 | Kangas | |
| 2,304,038 A * | 12/1942 | Thompson | B25B 23/0035 403/324 |
| 3,193,165 A | 7/1965 | Akhalaya et al. | |
| 3,245,703 A * | 4/1966 | Manly | F16L 37/0847 285/319 |

(Continued)

FOREIGN PATENT DOCUMENTS

| CA | 908529 A | 8/1972 |
|---|---|---|
| CN | 201481477 U | 5/2010 |

(Continued)

OTHER PUBLICATIONS

U.S. Appl. No. 14/591,193, filed Jan. 7, 2015, inventor: Sgroi, Jr.

(Continued)

*Primary Examiner* — Robert F Long
(74) *Attorney, Agent, or Firm* — Carter, DeLuca & Farrell LLP

(57) ABSTRACT

A loading unit and retention band assembly including a shell and a retention band. The shell has a proximal end portion that defines an engagement window and that includes an annular surface. The retention band is disposed radially about the annular surface of the proximal end portion and includes a resilient body having first and second ends. The first end includes a resilient lock that is configured to extend through the engagement window of the proximal end portion of the shell. The resilient lock is dimensioned to releasably engage a surgical instrument.

20 Claims, 6 Drawing Sheets

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev et al. | |
| 3,638,652 A | 2/1972 | Kelley | |
| 3,656,494 A * | 4/1972 | Cornett | E04H 15/60 135/114 |
| 3,735,450 A * | 5/1973 | Herubel | D01H 5/00 24/31 R |
| 3,753,582 A * | 8/1973 | Graham | F16L 37/0885 285/305 |
| 3,771,526 A | 11/1973 | Rudie | |
| 3,980,805 A * | 9/1976 | Lipari | H01R 24/40 174/88 C |
| 4,183,691 A * | 1/1980 | Van Melle | F16B 2/245 403/108 |
| 4,198,982 A | 4/1980 | Fortner et al. | |
| 4,207,898 A * | 6/1980 | Becht | A61B 17/115 227/179.1 |
| 4,255,143 A * | 3/1981 | Schuss | A61C 1/18 433/126 |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,627,761 A * | 12/1986 | Olson | B25B 23/0035 403/324 |
| 4,632,290 A | 12/1986 | Green et al. | |
| 4,646,745 A | 3/1987 | Noiles | |
| 4,647,241 A * | 3/1987 | Weber | F16B 7/0426 403/18 |
| 4,665,917 A * | 5/1987 | Clanton | A61B 17/115 606/153 |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,802,700 A * | 2/1989 | Stevenson | F16B 21/078 292/327 |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A * | 4/1992 | Main | A61B 17/115 227/175.1 |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,185,992 A * | 2/1993 | Garcia | A01B 1/227 56/400.04 |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,918 A * | 11/1993 | Phillips | A61B 17/29 606/1 |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,275,443 A * | 1/1994 | Klinger | F16L 37/144 285/305 |
| 5,282,810 A | 2/1994 | Allen et al. | |
| 5,285,944 A | 2/1994 | Green et al. | |
| 5,285,945 A | 2/1994 | Brinkerhoff et al. | |
| 5,291,910 A | 3/1994 | Bui | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A * | 11/1994 | Green | A61B 17/115 227/179.1 |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,405,175 A * | 4/1995 | Bonnah, II | F02M 55/004 24/DIG. 53 |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,481,949 A * | 1/1996 | Yen | B25B 23/0035 279/24 |
| 5,497,934 A | 3/1996 | Brady et al. | |
| 5,503,635 A * | 4/1996 | Sauer | A61B 17/1114 606/151 |
| 5,522,534 A | 6/1996 | Viola et al. | |
| 5,533,661 A | 7/1996 | Main et al. | |
| 5,560,257 A * | 10/1996 | DeBisschop | B62D 1/192 403/2 |
| 5,588,579 A | 12/1996 | Schnut et al. | |
| 5,593,187 A * | 1/1997 | Okuda | F16L 37/088 285/305 |
| 5,609,285 A | 3/1997 | Grant et al. | |
| 5,617,601 A * | 4/1997 | McDougall | A46B 13/008 15/22.1 |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |

(56) References Cited

U.S. PATENT DOCUMENTS

| | | | |
|---|---|---|---|
| 5,709,674 A * | 1/1998 | Steer | A61F 5/448 |
| | | | 604/332 |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,755,259 A * | 5/1998 | Schulze | F16K 17/30 |
| | | | 137/460 |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,954,448 A * | 9/1999 | Shim | H01R 33/7664 |
| | | | 403/291 |
| 5,957,363 A | 9/1999 | Heck | |
| 5,993,468 A | 11/1999 | Rygaard | |
| 6,024,748 A | 2/2000 | Manzo et al. | |
| 6,030,136 A * | 2/2000 | Bennett | A45D 40/06 |
| | | | 401/78 |
| 6,050,472 A | 4/2000 | Shibata | |
| 6,053,390 A | 4/2000 | Green et al. | |
| D425,784 S * | 5/2000 | Beugelsdyk | D8/395 |
| 6,056,070 A * | 5/2000 | Shinohara | B25D 9/145 |
| | | | 173/128 |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,254,305 B1 * | 7/2001 | Taylor | B25G 1/04 |
| | | | 15/144.4 |
| 6,258,107 B1 | 7/2001 | Balazs et al. | |
| 6,264,086 B1 | 7/2001 | McGuckin, Jr. | |
| 6,269,997 B1 | 8/2001 | Balazs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,539,920 B1 * | 4/2003 | Spiers | F02M 55/004 |
| | | | 123/456 |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,612,622 B2 * | 9/2003 | Andre | F16L 33/00 |
| | | | 285/305 |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,698,643 B2 | 3/2004 | Whitman | |
| 6,716,222 B2 | 4/2004 | McAlister et al. | |
| 6,716,233 B1 | 4/2004 | Whitman | |
| 6,726,697 B2 | 4/2004 | Nicholas et al. | |
| 6,736,031 B1 * | 5/2004 | Kang | B25B 7/12 |
| | | | 81/322 |
| 6,742,692 B2 | 6/2004 | Hartwick | |
| 6,743,244 B2 | 6/2004 | Blatter et al. | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,821,282 B2 | 11/2004 | Perry et al. | |
| 6,827,246 B2 | 12/2004 | Sullivan et al. | |
| 6,840,423 B2 | 1/2005 | Adams et al. | |
| 6,843,403 B2 | 1/2005 | Whitman | |
| 6,846,308 B2 | 1/2005 | Whitman et al. | |
| 6,852,122 B2 | 2/2005 | Rush | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,928,908 B1 * | 8/2005 | Yu | B25B 15/04 |
| | | | 81/177.4 |
| 6,938,814 B2 | 9/2005 | Sharma et al. | |
| 6,942,675 B1 | 9/2005 | Vargas | |
| 6,945,444 B2 | 9/2005 | Gresham et al. | |
| 6,953,138 B1 | 10/2005 | Dworak et al. | |
| 6,957,758 B2 | 10/2005 | Aranyi | |
| 6,959,851 B2 | 11/2005 | Heinrich | |
| 6,978,922 B2 | 12/2005 | Bilotti et al. | |
| 6,981,941 B2 | 1/2006 | Whitman et al. | |
| 6,981,979 B2 | 1/2006 | Nicolo | |
| 6,983,958 B2 * | 1/2006 | Rautureau | F16L 37/144 |
| | | | 285/305 |
| 7,032,798 B2 | 4/2006 | Whitman et al. | |
| 7,059,331 B2 | 6/2006 | Adams et al. | |
| 7,059,510 B2 | 6/2006 | Orban, III | |
| 7,077,856 B2 | 7/2006 | Whitman | |
| 7,080,769 B2 | 7/2006 | Vresh et al. | |
| 7,086,267 B2 | 8/2006 | Dworak et al. | |
| 7,114,642 B2 | 10/2006 | Whitman | |
| 7,118,528 B1 | 10/2006 | Piskun | |
| 7,122,044 B2 | 10/2006 | Bolduc et al. | |
| 7,128,748 B2 | 10/2006 | Mooradian et al. | |
| 7,141,055 B2 | 11/2006 | Abrams et al. | |
| 7,168,604 B2 | 1/2007 | Milliman et al. | |
| 7,179,267 B2 | 2/2007 | Nolan et al. | |
| 7,182,239 B1 | 2/2007 | Myers | |
| 7,195,142 B2 | 3/2007 | Orban, III | |
| 7,207,168 B2 | 4/2007 | Doepker et al. | |
| 7,220,237 B2 | 5/2007 | Gannoe et al. | |
| 7,229,105 B2 * | 6/2007 | Broersma | F16L 35/00 |
| | | | 124/49 |

(56) References Cited

U.S. PATENT DOCUMENTS

| | | | |
|---|---|---|---|
| 7,234,624 B2 | 6/2007 | Gresham et al. | |
| 7,235,089 B1 | 6/2007 | McGuckin, Jr. | |
| RE39,841 E | 9/2007 | Bilotti et al. | |
| 7,285,125 B2 | 10/2007 | Viola | |
| 7,300,077 B2 * | 11/2007 | Tawara | A47L 9/242 |
| | | | 285/417 |
| 7,303,106 B2 | 12/2007 | Milliman et al. | |
| 7,303,107 B2 | 12/2007 | Milliman et al. | |
| 7,309,341 B2 | 12/2007 | Ortiz et al. | |
| 7,322,994 B2 | 1/2008 | Nicholas et al. | |
| 7,325,713 B2 | 2/2008 | Aranyi | |
| 7,334,718 B2 | 2/2008 | McAlister et al. | |
| 7,335,212 B2 | 2/2008 | Edoga et al. | |
| 7,364,060 B2 | 4/2008 | Milliman | |
| 7,398,908 B2 | 7/2008 | Holsten et al. | |
| 7,399,305 B2 | 7/2008 | Csiky et al. | |
| 7,401,721 B2 | 7/2008 | Holsten et al. | |
| 7,401,722 B2 | 7/2008 | Hur | |
| 7,407,075 B2 | 8/2008 | Holsten et al. | |
| 7,410,086 B2 | 8/2008 | Ortiz et al. | |
| 7,422,137 B2 | 9/2008 | Manzo | |
| 7,422,138 B2 | 9/2008 | Bilotti et al. | |
| 7,431,191 B2 | 10/2008 | Milliman | |
| 7,438,718 B2 | 10/2008 | Milliman et al. | |
| 7,455,676 B2 | 11/2008 | Holsten et al. | |
| 7,455,682 B2 | 11/2008 | Viola | |
| 7,481,347 B2 | 1/2009 | Roy | |
| 7,494,038 B2 | 2/2009 | Milliman | |
| 7,497,479 B2 * | 3/2009 | Moessinger | F16L 19/005 |
| | | | 210/232 |
| 7,506,791 B2 | 3/2009 | Omaits et al. | |
| 7,516,877 B2 | 4/2009 | Aranyi | |
| 7,527,185 B2 | 5/2009 | Harari et al. | |
| 7,537,602 B2 | 5/2009 | Whitman | |
| 7,546,939 B2 | 6/2009 | Adams et al. | |
| 7,546,940 B2 | 6/2009 | Milliman et al. | |
| 7,547,312 B2 | 6/2009 | Bauman et al. | |
| 7,556,186 B2 | 7/2009 | Milliman | |
| 7,559,451 B2 | 7/2009 | Sharma et al. | |
| 7,562,442 B2 * | 7/2009 | Montena | H01R 43/04 |
| | | | 29/751 |
| 7,585,306 B2 | 9/2009 | Abbott et al. | |
| 7,588,174 B2 | 9/2009 | Holsten et al. | |
| 7,600,663 B2 | 10/2009 | Green | |
| 7,611,038 B2 | 11/2009 | Racenet et al. | |
| 7,635,385 B2 | 12/2009 | Milliman et al. | |
| 7,669,747 B2 | 3/2010 | Weisenburgh, II et al. | |
| 7,686,201 B2 | 3/2010 | Csiky | |
| 7,694,864 B2 | 4/2010 | Okada et al. | |
| 7,699,204 B2 | 4/2010 | Viola | |
| 7,708,181 B2 | 5/2010 | Cole et al. | |
| 7,717,313 B2 | 5/2010 | Criscuolo et al. | |
| 7,721,932 B2 | 5/2010 | Cole et al. | |
| 7,726,539 B2 | 6/2010 | Holsten et al. | |
| 7,743,958 E | 6/2010 | Orban, III | |
| 7,744,627 B2 | 6/2010 | Orban, III et al. | |
| 7,748,645 B2 * | 7/2010 | Breese | A01M 7/005 |
| | | | 180/315 |
| 7,770,776 B2 | 8/2010 | Chen et al. | |
| 7,771,440 B2 | 8/2010 | Ortiz et al. | |
| 7,776,060 B2 | 8/2010 | Mooradian et al. | |
| 7,793,813 B2 | 9/2010 | Bettuchi | |
| 7,802,712 B2 | 9/2010 | Milliman et al. | |
| 7,823,592 B2 | 11/2010 | Bettuchi et al. | |
| 7,837,079 B2 | 11/2010 | Holsten et al. | |
| 7,837,080 B2 | 11/2010 | Schwemberger | |
| 7,837,081 B2 | 11/2010 | Holsten et al. | |
| 7,845,536 B2 | 12/2010 | Viola et al. | |
| 7,845,538 B2 | 12/2010 | Whitman | |
| 7,857,187 B2 | 12/2010 | Willman | |
| 7,886,951 B2 | 2/2011 | Hessler | |
| 7,891,343 B2 * | 2/2011 | Braun | F02M 55/002 |
| | | | 123/446 |
| 7,896,215 B2 | 3/2011 | Adams et al. | |
| 7,900,806 B2 | 3/2011 | Chen et al. | |
| 7,909,039 B2 | 3/2011 | Hur | |
| 7,909,219 B2 | 3/2011 | Cole et al. | |
| 7,909,222 B2 | 3/2011 | Cole et al. | |
| 7,909,223 B2 | 3/2011 | Cole et al. | |
| 7,913,892 B2 | 3/2011 | Cole et al. | |
| 7,918,377 B2 | 4/2011 | Measamer et al. | |
| 7,922,062 B2 | 4/2011 | Cole et al. | |
| 7,922,743 B2 | 4/2011 | Heinrich et al. | |
| 7,931,183 B2 | 4/2011 | Orban, III | |
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 | 2/2012 | Milliman et al. | |
| 8,109,427 B2 | 2/2012 | Orban, III | |
| 8,113,406 B2 | 2/2012 | Holsten et al. | |
| 8,113,407 B2 | 2/2012 | Holsten et al. | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |

(56) References Cited

U.S. PATENT DOCUMENTS

| | | | |
|---|---|---|---|
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,250 B2 | 4/2014 | Bettuchi et al. | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 9,103,362 B2* | 8/2015 | Baro | A47B 49/006 |
| 9,113,885 B2* | 8/2015 | Hodgkinson | A61B 17/1114 |
| 9,504,470 B2* | 11/2016 | Milliman | A61B 17/07292 |
| 9,506,592 B2* | 11/2016 | Turnau, III | F16L 37/0915 |
| 9,757,133 B2* | 9/2017 | Latimer | A61B 90/30 |
| 9,845,907 B2* | 12/2017 | Hess | F16L 37/1225 |
| 9,913,643 B2* | 3/2018 | Penna | A61B 17/072 |
| 10,278,886 B2* | 5/2019 | Fong | A61H 3/02 |
| 2003/0111507 A1 | 6/2003 | Nunez | |
| 2004/0059227 A1 | 3/2004 | Nita et al. | |
| 2004/0194324 A1 | 10/2004 | Youn-Chyuan | |
| 2005/0051597 A1 | 3/2005 | Toledano | |
| 2005/0107813 A1 | 5/2005 | Gilete Garcia | |
| 2005/0123344 A1* | 6/2005 | Bensussan | F16B 7/042 |
| | | | 403/109.2 |
| 2005/0236459 A1* | 10/2005 | Gresham | A61B 46/27 |
| | | | 227/175.1 |
| 2006/0000869 A1 | 1/2006 | Fontayne | |
| 2006/0011698 A1 | 1/2006 | Okada et al. | |
| 2006/0101600 A1* | 5/2006 | Weaver | B25G 3/26 |
| | | | 15/145 |
| 2006/0201989 A1 | 9/2006 | Ojeda | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0103510 A1* | 5/2008 | Taylor | A61B 17/08 |
| | | | 606/143 |
| 2008/0179375 A1 | 7/2008 | Scirica | |
| 2008/0251561 A1* | 10/2008 | Eades | B25C 1/14 |
| | | | 227/10 |
| 2008/0281299 A1* | 11/2008 | Menn | A61B 1/0014 |
| | | | 606/1 |
| 2008/0308605 A1 | 12/2008 | Scirica | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0326540 A1 | 12/2009 | Estes | |
| 2010/0019016 A1 | 1/2010 | Edoga et al. | |
| 2010/0051668 A1 | 3/2010 | Milliman et al. | |
| 2010/0084453 A1 | 4/2010 | Hu | |
| 2010/0093205 A1* | 4/2010 | Stone | H01R 13/633 |
| | | | 439/352 |
| 2010/0147923 A1 | 6/2010 | D'Agostino et al. | |
| 2010/0163598 A1 | 7/2010 | Belzer | |
| 2010/0224668 A1 | 9/2010 | Fontayne et al. | |
| 2010/0230465 A1 | 9/2010 | Smith et al. | |
| 2010/0253065 A1* | 10/2010 | Lotti | F16L 33/227 |
| | | | 285/3 |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0101066 A1* | 5/2011 | Farascioni | A61B 17/07207 |
| | | | 227/175.2 |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0186614 A1 | 8/2011 | Kasvikis | |
| 2011/0192882 A1 | 8/2011 | Hess et al. | |
| 2011/0205072 A1* | 8/2011 | Ben-Mansour | G01M 3/183 |
| | | | 340/605 |
| 2011/0276036 A1 | 11/2011 | Spranger et al. | |
| 2012/0061448 A1 | 3/2012 | Zingman | |
| 2012/0116363 A1* | 5/2012 | Houser | A61B 18/1206 |
| | | | 606/1 |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0234894 A1* | 9/2012 | Kostrzewski | A61B 17/07207 |
| | | | 227/175.2 |
| 2012/0234896 A1* | 9/2012 | Ellerhorst | A61B 17/07207 |
| | | | 227/176.1 |
| 2012/0273548 A1 | 11/2012 | Ma et al. | |
| 2012/0273550 A1* | 11/2012 | Scirica | A61B 17/07207 |
| | | | 227/176.1 |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |
| 2013/0032628 A1 | 2/2013 | Li et al. | |
| 2013/0056516 A1 | 3/2013 | Viola | |
| 2013/0060258 A1 | 3/2013 | Giacomantonio | |
| 2013/0096591 A1 | 4/2013 | Hart et al. | |
| 2013/0105544 A1 | 5/2013 | Mozdzierz et al. | |
| 2013/0105546 A1 | 5/2013 | Milliman et al. | |
| 2013/0105551 A1 | 5/2013 | Zingman | |
| 2013/0123705 A1 | 5/2013 | Holm et al. | |
| 2013/0126580 A1 | 5/2013 | Smith et al. | |
| 2013/0153630 A1 | 6/2013 | Miller et al. | |
| 2013/0153631 A1 | 6/2013 | Vasudevan et al. | |
| 2013/0153633 A1 | 6/2013 | Casasanta, Jr. et al. | |
| 2013/0153634 A1 | 6/2013 | Carter et al. | |
| 2013/0153638 A1 | 6/2013 | Carter et al. | |
| 2013/0153639 A1 | 6/2013 | Hodgkinson et al. | |
| 2013/0158566 A1* | 6/2013 | Harris | A61B 17/1285 |
| | | | 606/142 |
| 2013/0167365 A1* | 7/2013 | Herren | F16L 55/1157 |
| | | | 29/700 |
| 2013/0175315 A1 | 7/2013 | Milliman | |
| 2013/0175318 A1 | 7/2013 | Felder et al. | |
| 2013/0175319 A1 | 7/2013 | Felder et al. | |
| 2013/0175320 A1 | 7/2013 | Mandakolathur Vasudevan et al. | |
| 2013/0181029 A1 | 7/2013 | Milliman | |
| 2013/0181035 A1 | 7/2013 | Milliman | |
| 2013/0181036 A1 | 7/2013 | Olson et al. | |
| 2013/0186930 A1 | 7/2013 | Wenchell et al. | |
| 2013/0193185 A1 | 8/2013 | Patel | |
| 2013/0193187 A1 | 8/2013 | Milliman | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0200131 A1 | 8/2013 | Racenet et al. | |
| 2013/0200607 A1* | 8/2013 | Rodenberg | F16L 37/0915 |
| | | | 285/82 |
| 2013/0206816 A1 | 8/2013 | Penna | |
| 2013/0214027 A1 | 8/2013 | Hessler et al. | |
| 2013/0214028 A1 | 8/2013 | Patel et al. | |
| 2013/0228609 A1 | 9/2013 | Kostrzewski | |
| 2013/0240597 A1 | 9/2013 | Milliman et al. | |
| 2013/0240600 A1 | 9/2013 | Bettuchi | |

(56) References Cited

U.S. PATENT DOCUMENTS

| | | |
|---|---|---|
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0001236 A1 | 1/2014 | Shelton, IV et al. |
| 2014/0008413 A1 | 1/2014 | Williams |
| 2014/0012317 A1 | 1/2014 | Orban et al. |
| 2014/0025071 A1* | 1/2014 | Sims ............... A61B 17/2812 606/46 |
| 2014/0309677 A1 | 10/2014 | Baldwin |
| 2014/0312095 A1* | 10/2014 | Scirica ............. A61B 17/068 227/176.1 |
| 2015/0108201 A1 | 4/2015 | Williams |
| 2015/0320420 A1 | 11/2015 | Penna et al. |
| 2015/0351769 A1* | 12/2015 | Lee ................. A61B 17/1155 227/179.1 |
| 2016/0000428 A1* | 1/2016 | Scirica .................. A61B 1/32 227/180.1 |
| 2016/0157856 A1* | 6/2016 | Williams ........... A61B 17/068 227/175.1 |
| 2016/0175026 A1* | 6/2016 | Bhagat ............... A61B 17/29 606/52 |
| 2016/0192934 A1* | 7/2016 | Williams ........... A61B 17/105 227/176.1 |
| 2016/0192938 A1* | 7/2016 | Sgroi, Jr. .......... A61B 17/1155 227/175.1 |
| 2016/0245443 A1* | 8/2016 | Zonneveld ........... F16L 37/18 |
| 2017/0079660 A1* | 3/2017 | Sgroi ................ A61B 17/105 |
| 2017/0198887 A1* | 7/2017 | Veloskey .............. F21V 17/02 |

FOREIGN PATENT DOCUMENTS

| | | |
|---|---|---|
| CN | 203379172 U | 1/2014 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 0154594 A1 | 8/2001 |
| WO | 2004107990 A1 | 12/2004 |
| WO | 2008107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

U.S. Appl. No. 14/810,811, filed Jul. 28, 2015, inventor: Sgroi, Jr., et al.
U.S. Appl. No. 14/805,547, filed Jul. 22, 2015, inventor: Scirica, et al.
U.S. Appl. No. 14/859,590, filed Sep. 21, 2015, inventor: Sgroi.
U.S. Appl. No. 62/100,512, filed Jan. 7, 2015, inventor: Williams et al.
U.S. Appl. No. 62/150,913, filed Apr. 22, 2015, inventor: Penna et al.
European Search Report dated May 10, 2016, issued in EP Application No. 15 19 8203.
European Search Report dated May 17, 2016, issued in EP Application No. 16150284.
European Search Report dated Jun. 24, 2016, issued in EP Application No. 16150288.5.
European Search Report dated Sep. 1, 2016, issued in EP 16166326.
European Search Report dated Nov. 30, 2016, issued in EP Application No. 16181395.
Partial European Search Report dated Jan. 16, 2017, issued in EP Appln. No. 16180339.
European Search Report dated May 23, 2017, issued in EP Application No. 16189648.
EP Examination Report dated Jun. 20, 2017, issued in EP Application No. 16150288.
Chinese Office Action dated Jan. 19, 2020, issued in CN Appln. No. 201510897764, seven pages.
Chinese Office Action dated Jun. 10, 2019, issued in CN Appln. Serial No. 201510897764.

* cited by examiner

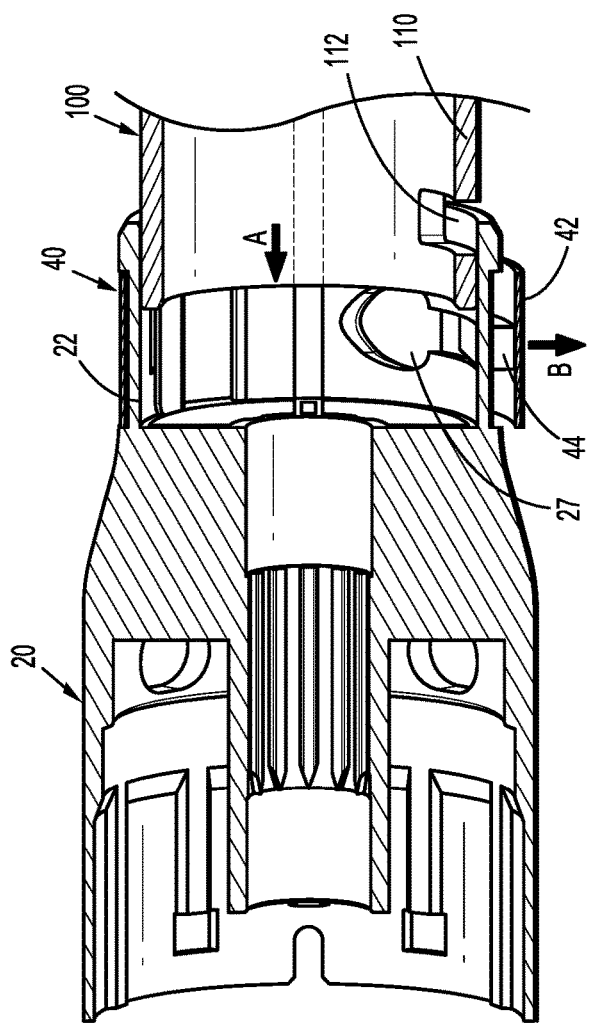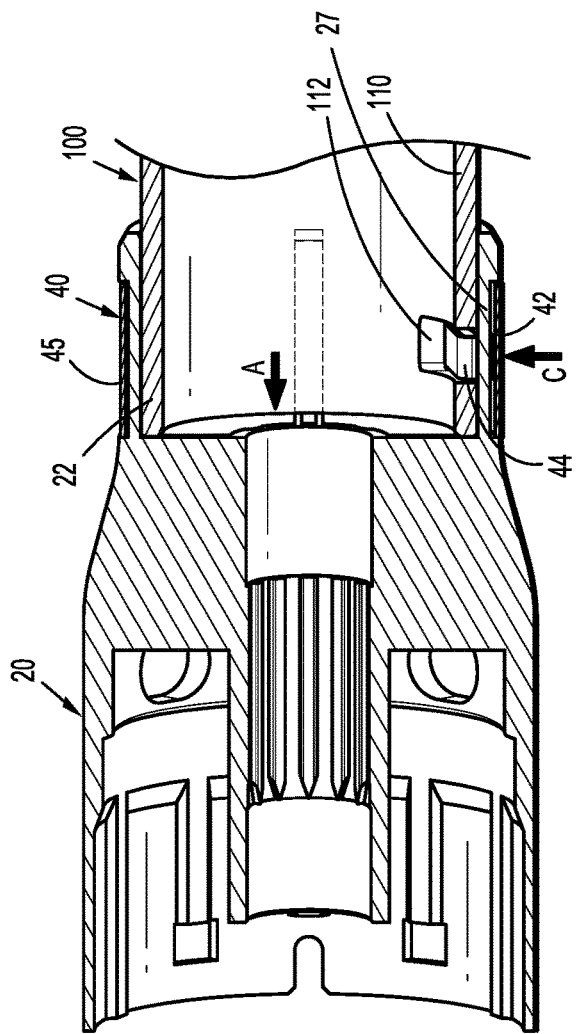

LOADING UNIT ATTACHMENT BAND FOR SURGICAL STAPLING INSTRUMENT

CROSS-REFERENCE TO RELATED APPLICATIONS

This application is a divisional of U.S. patent application Ser. No. 14/804,814, filed Jul. 21, 2015, which claims the benefit of and priority to U.S. Provisional Patent Application Ser. No. 62/088,729, filed Dec. 8, 2014, the entire disclosure of which is incorporated by reference herein.

BACKGROUND

1. Technical Field

The present disclosure relates generally to surgical stapling instruments. More specifically, the present disclosure relates to circular stapling instruments having replaceable loading units.

2. Background of Related Art

Surgical stapling instruments configured to join tissue portions during a surgical procedure are well known. These instruments include linear end effectors which are oriented parallel or transverse to a longitudinal axis of the instrument. These instruments also include circular end effectors. Typically, the linear stapling instruments include a disposable loading unit or a replaceable cartridge that allows the stapling instrument to be used multiple times. In contrast, conventional circular stapling instruments typically include a cartridge or shell assembly that is fixedly attached to the instrument such that the instrument must be disposed of after a single use.

A need exists in the art for a simple, inexpensive instrument for releasably, but securely, fastening a cartridge or shell assembly to a circular stapling instrument to facilitate reuse of the stapling instrument.

SUMMARY

In an aspect of the present disclosure, a loading unit and retention band assembly including a shell and a retention band. The shell has a proximal end portion that defines an engagement window and that includes an annular surface. The retention band is disposed radially about the annular surface of the proximal end portion and includes a resilient body having first and second ends. The first end includes a resilient lock that is configured to extend through the engagement window of the proximal end portion of the shell. The resilient lock is dimensioned to releasably engage a surgical instrument.

In aspects, the shell includes a distal end portion that supports a staple cartridge. The annular surface may define an annular groove and the body of the retention band may be disposed within the annular groove.

In some aspects, the resilient lock of the retention band may extend through the engagement window towards a longitudinal axis of the shell. The proximal end portion of the shell may define a clip opening that is radially offset from the engagement window. The second end of the retention band may include a clip that extends through the clip opening and captures a portion of the proximal end portion of the shell between the clip and the body of the retention band. The proximal end portion of the shell may define a tab opening. The clip opening may be positioned between the engagement window and the tap opening. The retention band may include a tap adjacent the second end of the body that extends from the body towards the clip. The tab may extend through the tap opening to fix the second end of the retention band relative to the proximal end portion. The resilient body of the retention band may be configured to urge the first and second ends towards one another.

In another aspect of the present disclosure, a surgical instrument and loading unit assembly includes a loading unit, a surgical instrument, and a retention band. The loading unit includes a shell that has a proximal end portion that includes an annular surface and that defines an engagement window. The surgical instrument has a distal end that is received within the proximal end portion of the shell. The retention band is disposed radially about the annular surface of the proximal end portion. The retention band has a resilient body that includes first and second ends. The first end includes a resilient lock that extends through the engagement window of the proximal end portion of the shell to releasably couple the loading unit to the surgical instrument.

In aspects, the distal end of the surgical instrument defines an attachment window. The resilient lock of the retention band may extend through the engagement and attachment windows to releasably couple the loading unit to the surgical instrument. The shell may define a longitudinal axis and the proximal end portion of the shell may include a key that protrudes inward from the proximal end portion. The distal end of the surgical instrument defines a keyway which receives the key to radially fix the loading unit and the surgical instrument relative to one another. The key may be positioned about the proximal end portion of the loading unit and the keyway may be positioned about the distal end of the surgical instrument to radially align the engagement window of the loading unit with the attachment window of the surgical instrument.

In another aspect of the present disclosure, a method of securing a loading unit to a surgical instrument includes inserting a distal end of the surgical instrument into a proximal end portion of the loading unit, deforming a retention band that is disposed on the proximal end portion of the loading unit to allow the loading unit to fully receive the distal end of the surgical instrument, and releasing the retention band when the distal end of the surgical instrument is fully received within the proximal end portion of the loading unit to secure the loading unit to the surgical instrument.

In aspects, the method includes attaching the retention band to the proximal end portion of the loading unit. Attaching the retention band to the proximal end portion of the loading unit may precede inserting a distal end of the surgical instrument into the proximal end portion of the loading unit.

In some aspects, attaching the retention band to the proximal end portion of the loading unit includes securing a second end of the retention band to the proximal end portion of the loading unit and positioning a body of the retention band within an annular groove defined in the proximal end portion of the loading unit. The body of the retention band may be positioned between the first and second ends of the retention band. Securing the second end of the retention band to the proximal end portion of the loading unit may include capturing a portion of the proximal end portion between a clip extending from the section end of the retention band and the body of the retention band. Capturing the portion of the proximal end portion may include rotating the retention band in a first direction unit a tab adjacent the second end of the retention band that is disposed within a tab opening defined in the proximal end portion. The tab may engage the tab opening to prevent the retention band from rotating in a second direction opposite the first direction.

In particular aspects, positioning the body of the retention band within the annular groove includes positioning a lock of the retention band through an engagement window formed in the proximal end portion of the loading unit after positioning the body of the retention band. Positioning the lock of the retention band through the engagement window may include a radiating portion of the lock engaging an end surface of the engagement window that is spaced apart from the first end of the retention band to prevent the retention band from rotating in the second direction.

In certain aspects, the method includes separating the loading unit from the surgical instrument after releasing the first end of the retention tab. Separating the loading unit from the adapter may include deforming the retention band to permit the distal end of the surgical instrument to release the proximal end portion of the loading unit and withdrawing the distal end of the surgical instrument from within the proximal end portion of the loading unit.

In aspects, inserting the distal end of the surgical instrument into the proximal end portion of the loading unit includes the distal end abutting a lock of the retention band that extends through an engagement window of the proximal end portion. Deforming the first end of the retention band may include removing the lock from the engagement window. Releasing the first end of the retention band when the distal end of the surgical instrument is fully received within the proximal end portion of the loading unit may include the lock of the retention band that extends through the engagement window that is formed in the proximal end portion of the shell. The attachment window may be formed in the distal end of the surgical instrument to secure the loading unit to the surgical instrument.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein:

FIG. 11 is a side cross-sectional view with of the loading unit and surgical instrument of FIG. 10 with a portion of the retention band deformed; and FIG. 12 is a side cross-sectional view of the loading unit and the surgical instrument of FIG. 11 coupled together.

DETAILED DESCRIPTION OF EMBODIMENTS

Figure 1:
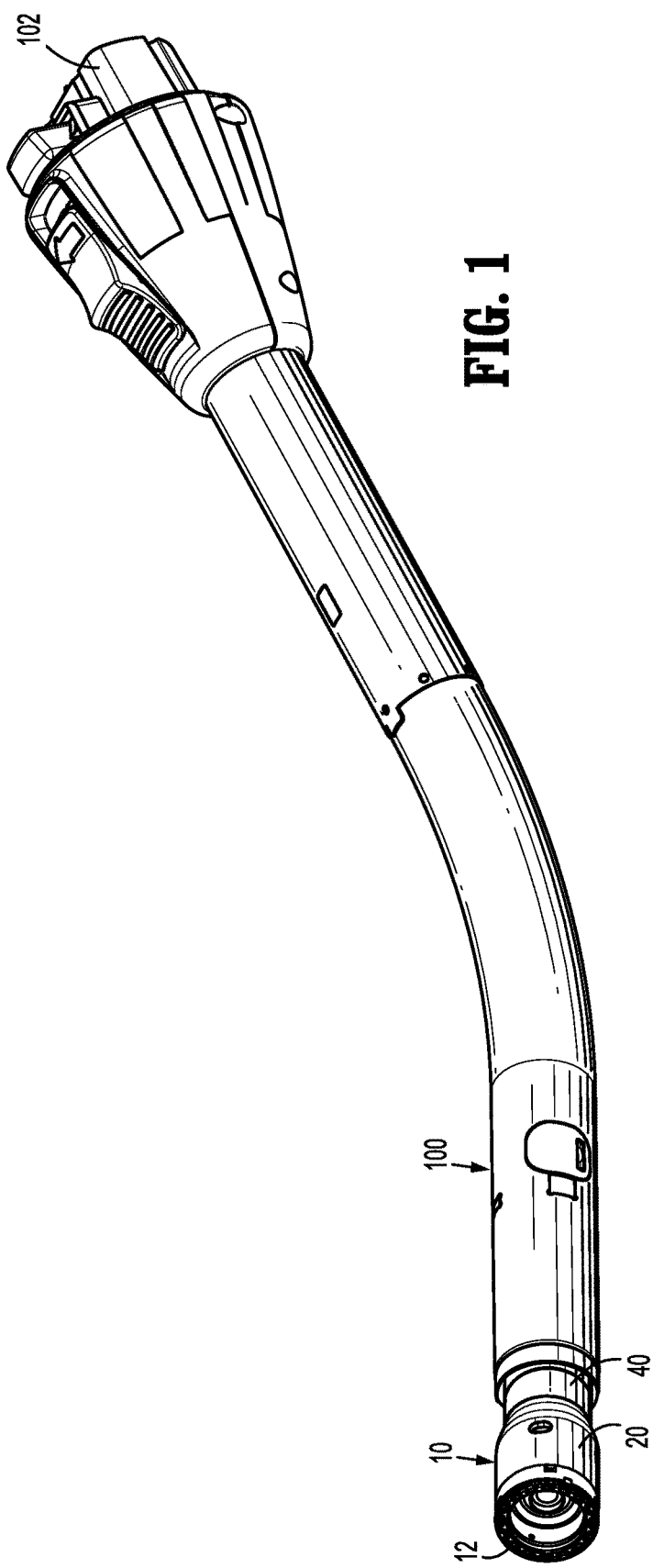
FIG. 1 is a perspective view of a circular stapling surgical instrument in accordance with the present disclosure with a loading unit releasably coupled to a distal end of the surgical instrument.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the instrument or component thereof that is closest to the clinician and the term "distal" refers to the portion of the instrument or component thereof that is farthest from the clinician.

Figure 2:
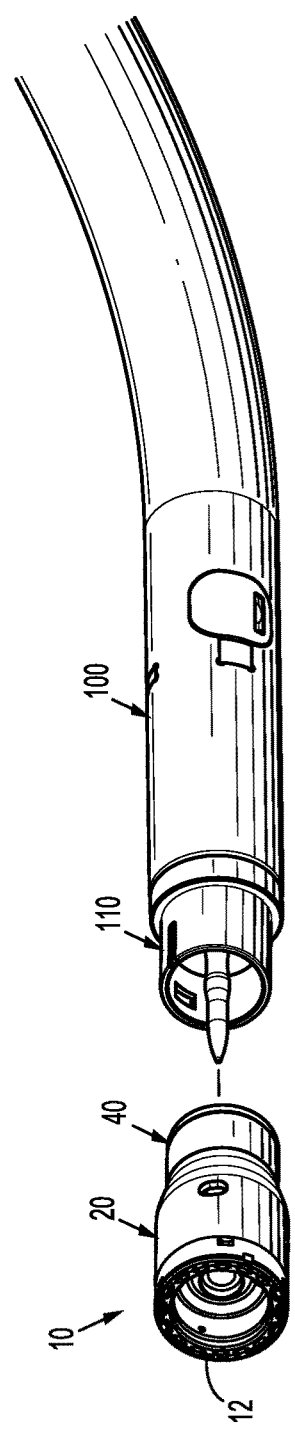
FIG. 2 is a perspective view of the adapter of FIG. 1 with the loading unit decoupled from the surgical instrument.

FIGS. 1 and 2 illustrate a loading unit 10 and an adapter 100 in accordance with an embodiment of the present disclosure. The loading unit 10 is configured for selective connection to a powered hand held electromechanical instrument (not shown) via the adapter 100. Alternatively, the loading unit 10 can be configured for connection to a manually actuated handle assembly or stapling instrument such as described in U.S. Pat. No. 8,789,737 ("the '737 Patent"), which is incorporated herein by reference. In such an embodiment, an elongated body portion of the stapling instrument may have a configuration similar to that of the adapter 100 as shown in FIG. 2. In the illustrated embodiment, the loading unit 10 is releasably coupled to a distal end portion 110 of the adapter 100 and includes a staple cartridge 12, a shell assembly 20, and an attachment member or retention band 40 for releasably securing the loading unit 10 to the adapter 100. The loading unit 10 may also include an anvil (not shown). The adapter 100 is configured to translate movement of a stapling instrument, e.g., an electromechanical instrument (not shown), to actuate the staple cartridge 12 to suture and cut tissue (not shown). A proximal end 102 of the adapter 100 is attachable to the stapling instrument to actuate the staple cartridge 12. It is contemplated that the proximal end 102 of the adapter 100 may be attached to a manually actuated instrument such as described in the '737 Patent to actuate the staple cartridge 12.

For a detailed description of the structure and function of an exemplary adapter and loading unit, please refer to commonly owned U.S. Provisional Patent Application Ser. No. 62/066,518, filed on Oct. 21, 2014. For a detailed description of the structure and function of an exemplary electromechanical instrument, please refer to commonly owned U.S. patent application Ser. No. 13/484,975, filed on May 31, 2012, now published as U.S. Patent Publication No. 2012/0253329. Each of these applications is incorporated herein by reference in its entirety.

Figure 3:
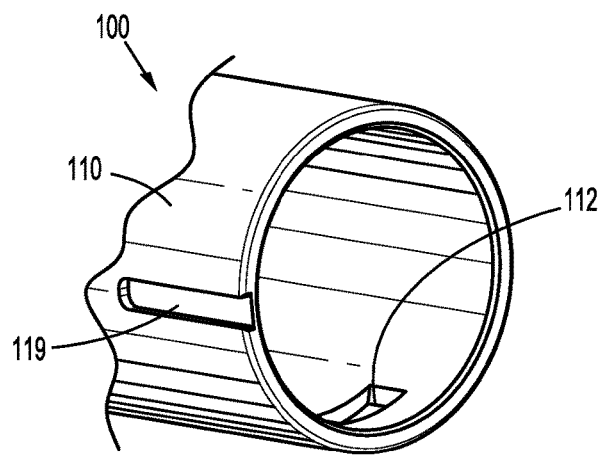
FIG. 3 is an enlarged perspective view of a portion of the distal end of the surgical instrument of FIG. 2.

With reference to FIG. 3, the distal end 110 of the adapter 100 defines an attachment window 112 and a keyway 119. The attachment window 112 extends through the adapter 100 and is configured to interact with the retention band 40 to longitudinally fix the shell assembly 20 to the distal end 110 of the adapter 100 as detailed below. The keyway 119 is defined in the outer surface of the distal end 110 of the adapter 100 and extends parallel to a longitudinal axis of the adapter 100. The keyway 119 is sized and configured to radially align and fix the shell assembly 20 to the adapter 100 as detailed below. As shown, the keyway 119 does not pass entirely through the distal end 110 of the adapter 100; however, it is contemplated that the keyway 119 may pass entirely through the distal end 110 of the adapter 100 to form a longitudinal slot in the distal end 110 of the adapter 100.

Figure 4:
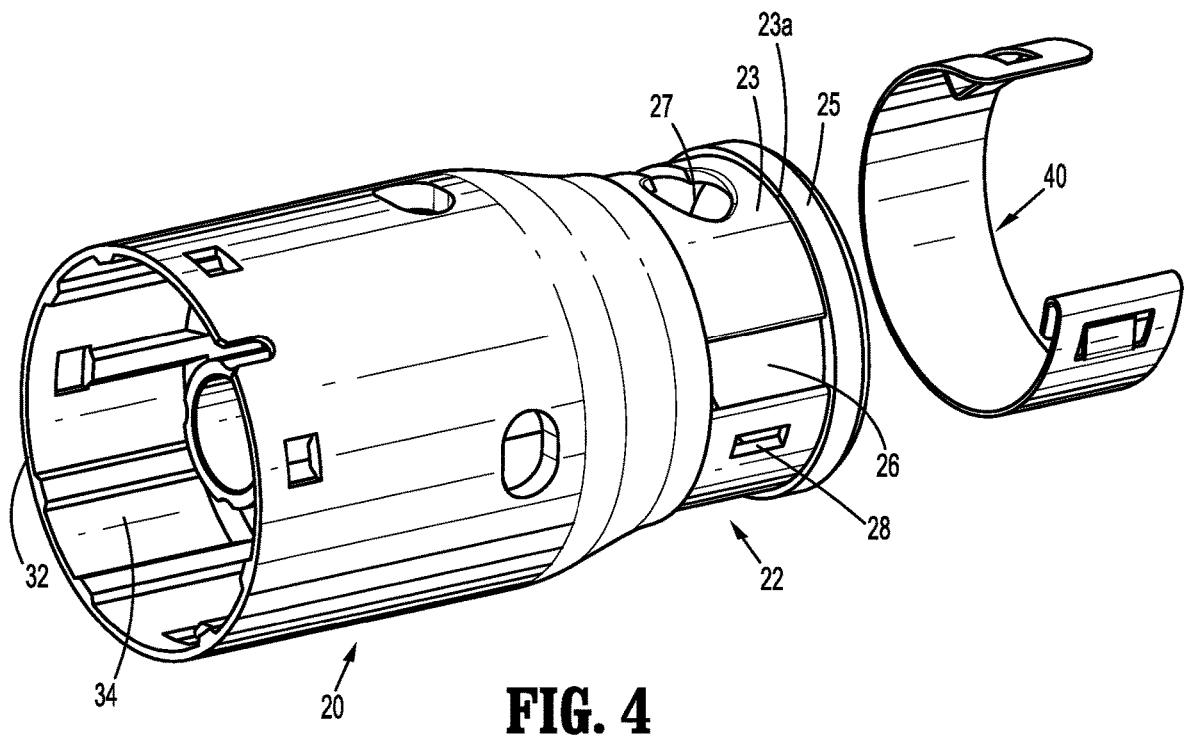
FIG. 4 is a perspective view of the loading unit of FIG. 3 with a retention band separated from the shell assembly.
Figure 5:
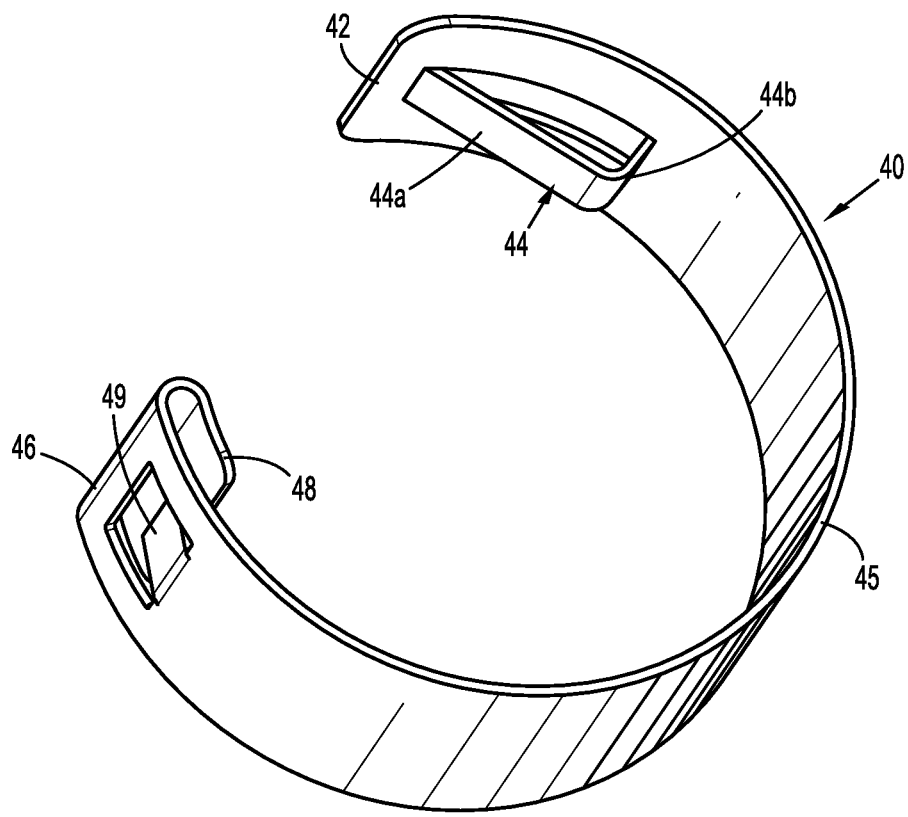
FIG. 5 is a perspective view of the retention band of FIG. 4.
Figure 6:
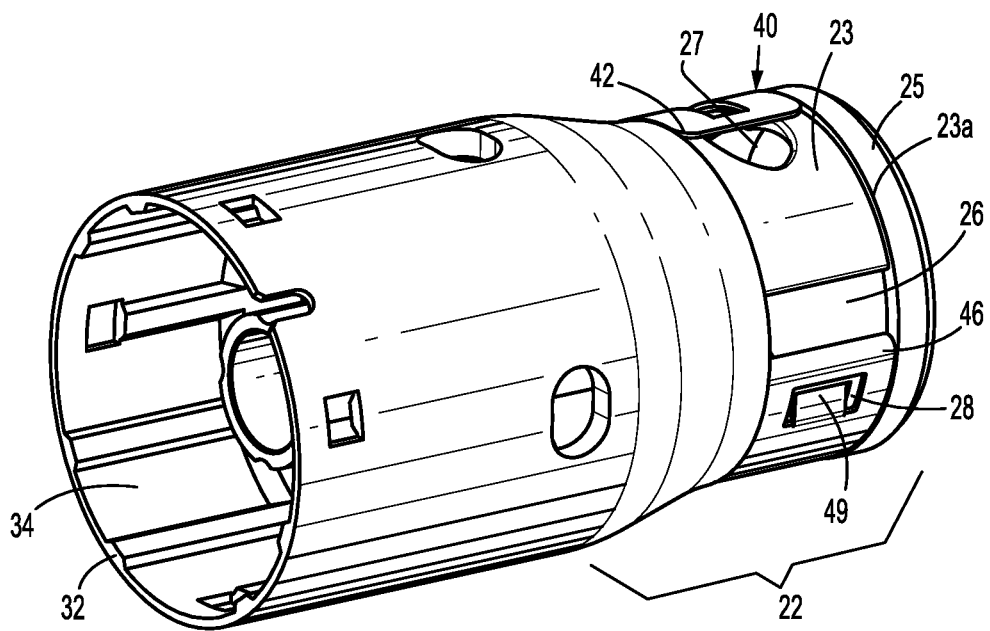
FIG. 6 is an enlarged perspective view of the loading unit of FIG. 2 with a staple cartridge removed from a shell assembly of the loading unit.

Referring to FIGS. 4-6, the shell assembly 20 includes a proximal end portion 22 that defines an opening 24 (FIG. 7) shaped to receive the distal end 110 (FIG. 2) of the adapter 100 and a distal end 32 that defines a receptacle 34 for selectively receiving the staple cartridge 12 (FIG. 2). In embodiments, the opening 24 and the receptacle 34 have a cylindrical shape. The proximal end portion 22 of the shell assembly 20 includes an annular surface 23 that defines an annular groove 23a. The annular groove 23a receives the attachment member or retention band 40 to releasably secure the shell assembly 20 to the adapter 100. The radial groove 23a may be sized to receive the retention band 40 such that the retention band 40 forms a continuous surface with an outer surface of the proximal end portion 22 of the shell assembly 20. The proximal end portion 22 includes a proximal ring 25 positioned at a proximal end of the annular surface 23 and defines a clip opening 26, an engagement window 27, and a tab opening 28 that extends through the annular surface 23. The engagement window 27 and the tab opening 28 are radially spaced apart from one another along the annular surface 23 with the clip opening 26 positioned therebetween.

Figure 7:
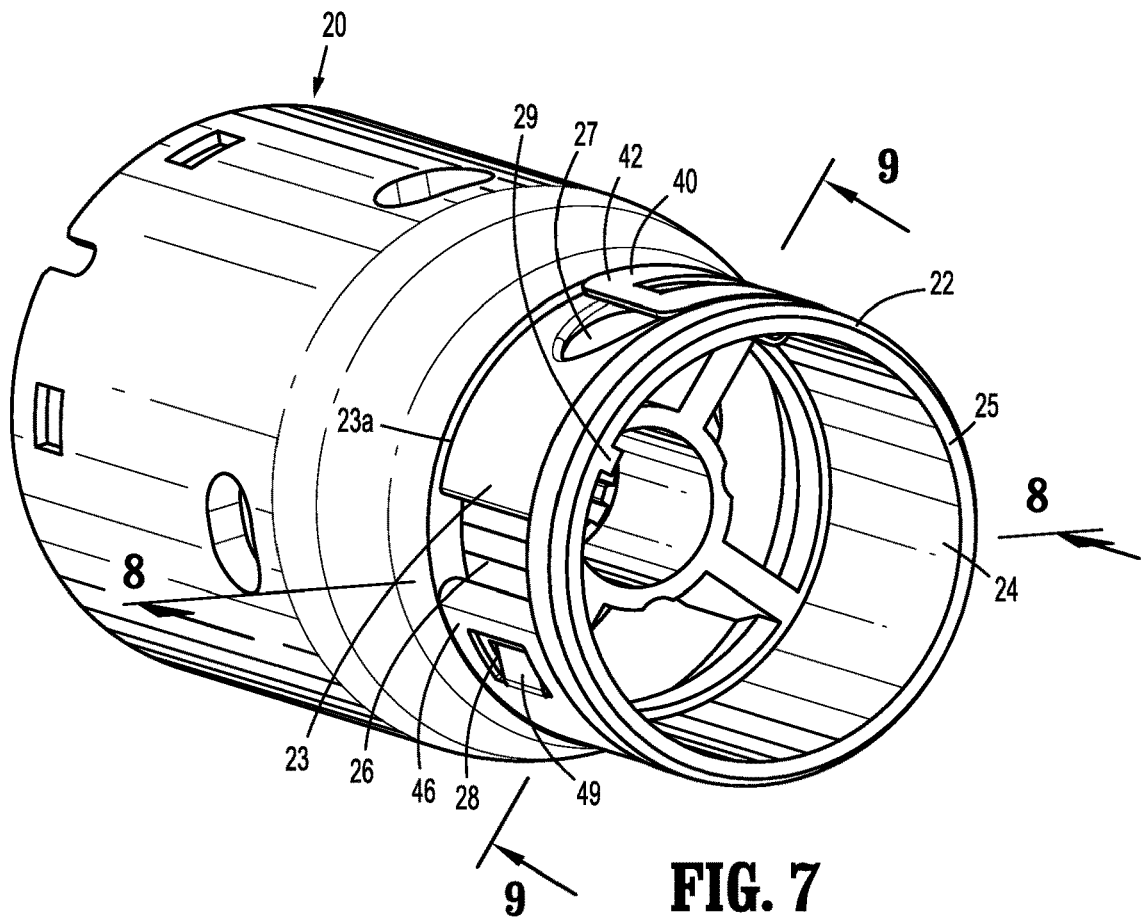
FIG. 7 is a rear perspective view of the loading unit of FIG. 4.
Figure 8:
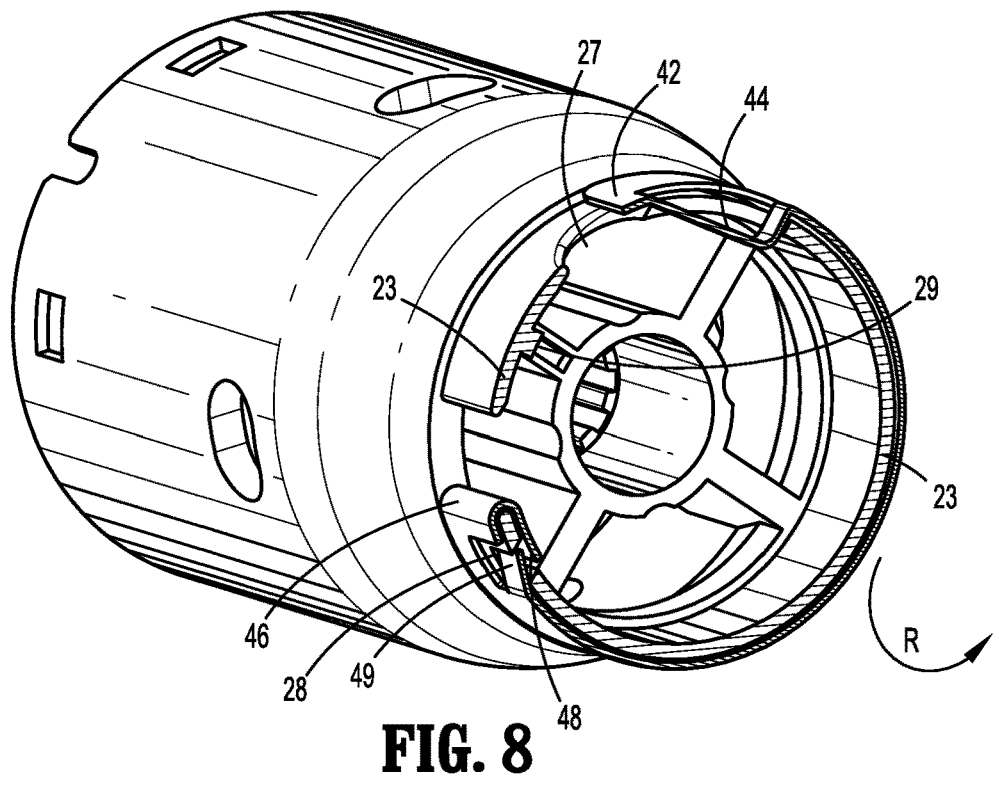
FIG. 8 is a cross-sectional view taken along the section line 8-8 of FIG. 7.

Referring briefly to FIGS. 7 and 8, the proximal end portion 22 of the shell assembly 20 includes a key 29 which protrudes from an inner surface of the proximal end portion 22 and extends towards a longitudinal axis of the shell assembly 20. In embodiments, the key 29 extends in a direction parallel to the longitudinal axis of the shell assembly 20 and is positioned between the engagement window 27 and the clip opening 26. It is contemplated that the key 29 may be positioned anywhere about the inner surface of the proximal end portion 22 of the shell assembly 20 and may extend proximally from a position within the annular surface 23 and onto the inner surface of the proximal ring 25 as shown in FIG. 7.

Referring again to FIGS. 4-6, the retention band 40 includes a body 45 having first and second ends 42, 46. The first end 42 includes a lock 44 that is sized to be received within the engagement window 27 of the shell assembly 20. The lock 44 includes a tapered portion 44a adjacent the first end 42 and a radial portion 44b adjacent the body 45. The second end 46 is bent backwards to form a clip 48. The second end 46 also includes an inwardly extending, resilient tab 49 which extends towards the clip 48. The clip 48 is sized to pass through the clip opening 26 formed in the proximal end portion 22 of the shell assembly 20 and to capture a portion of the annular surface 23 of the proximal end portion 22 between the clip 48 and the body 45 of the band 40. The tab 49 is sized to be received within the tab opening 28 defined in the annular surface 23 to secure the second end 46 of the retention band 40 to the shell assembly 20.

Referring also to FIGS. 7 and 8, the retention band 40 is attached to the shell assembly 20 by positioning the body 45 of the retention band 40 about the annular surface 23 of the proximal end portion 22 of the shell assembly 20 and inserting second end 46 of the retention band 40 into the clip opening 26 defined through the annular surface 23. The clip 48 is positioned such that a portion of the annular surface 23 is captured between the clip 48 and the body 45 of the retention band 40. The retention band 40 is rotated in a first direction as shown by Arrow R (FIG. 8) until the portion of the annular surface 23 abuts the second end 46 of the retention band 40 between the clip 48 and the body 45. As the portion of the annular surface 23 moves into abutment with the second end 46 of the retention band 40, the tab 49 snaps through the tab opening 28 to secure the second end 46 of the retention band 40 to the shell assembly 20. More specifically, as the retention band 40 is rotated in the first direction indicated by Arrow R, the tab 49 is urged away from the longitudinal axis of the shell assembly 20 by engagement with the annular surface 23 until the tab 48 passes over and snaps into the tab opening 28. When the tab 48 is positioned within the tab opening 28, the tab 48 prevents the retention band 40 from rotating in a second direction opposite the first direction via engagement of the tab 48 with the portion of the proximal end portion 22 of the shell assembly 20 captured between the clip 49 and the tab 48.

When the second end 46 of the retention band 40 is secured to the shell assembly 20, the body 45 of the retention band 40 is positioned within the groove 23a defining annular surface 23 such that the body 45 is in contact with the annular surface 23. In this position, the lock 44 on the first end 42 of the retention band 40 passes through the engagement window 27. When the lock 44 is positioned within the engagement window 27, the radial portion 44b of the lock 44 engages a portion of the proximal end portion 22 defining the engagement window 27 to prevent the retention band 40 from rotating in the second direction. In embodiments, the body 45 of the retention band 40 is formed of a resilient material which is flexed outwardly when positioned about the proximal end portion 22 of the shell assembly 20. As such, the resilience of the body 45 urges the first and second ends 42, 46 of the retention band 40 towards one another. This biasing of the body 45 assists in securing the retention band 40 to the shell assembly 20.

Figure 9:
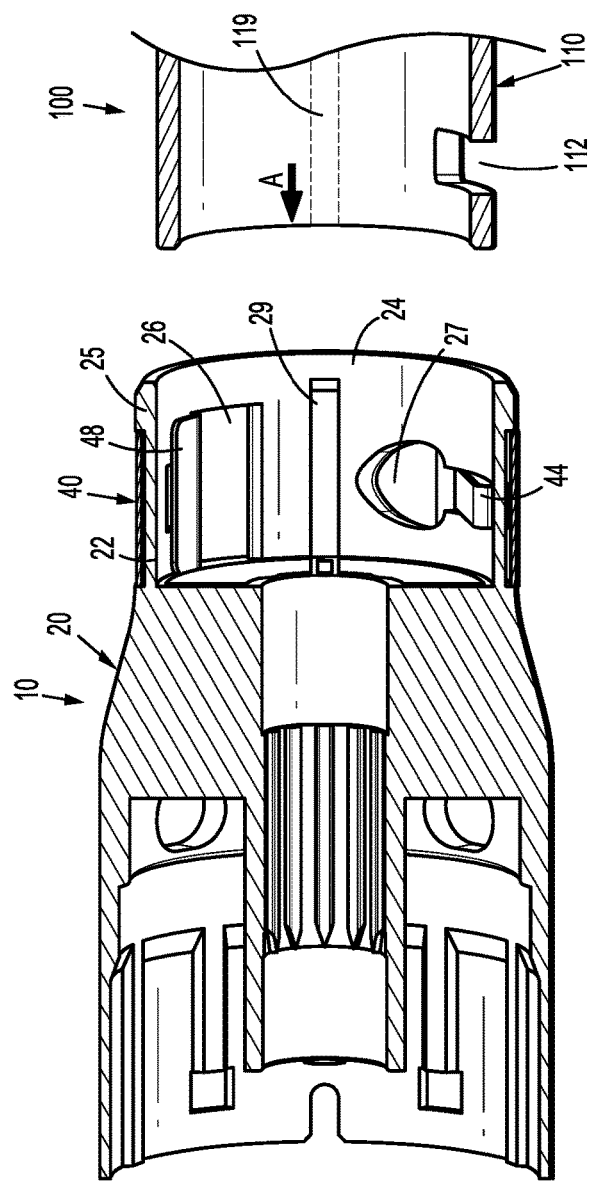
FIG. 9 is a side cross-sectional view taken along the section line 9-9 of FIG. 7 and a portion of the adapter of FIG. 2.

Referring to FIGS. 9-12, to secure the loading unit 10 to the distal end 110 of the adapter 100 or an elongated body of a manually actuated surgical instrument, the longitudinal axis of the shell assembly 20 is aligned with the longitudinal axis of the adapter 100 as shown in FIG. 9. In addition, the proximal end portion 22 of the shell assembly 20 is radially aligned with the distal end 110 of the adapter 100 such that the key 29 of the shell assembly 20 is aligned with the keyway 119 of the adapter 100. It will be appreciated that when the key 29 is aligned with the keyway 119, the attachment window 112 of the adapter 100 is aligned with the engagement window 27 of the shell assembly 20 (FIG. 9).

Figure 10:
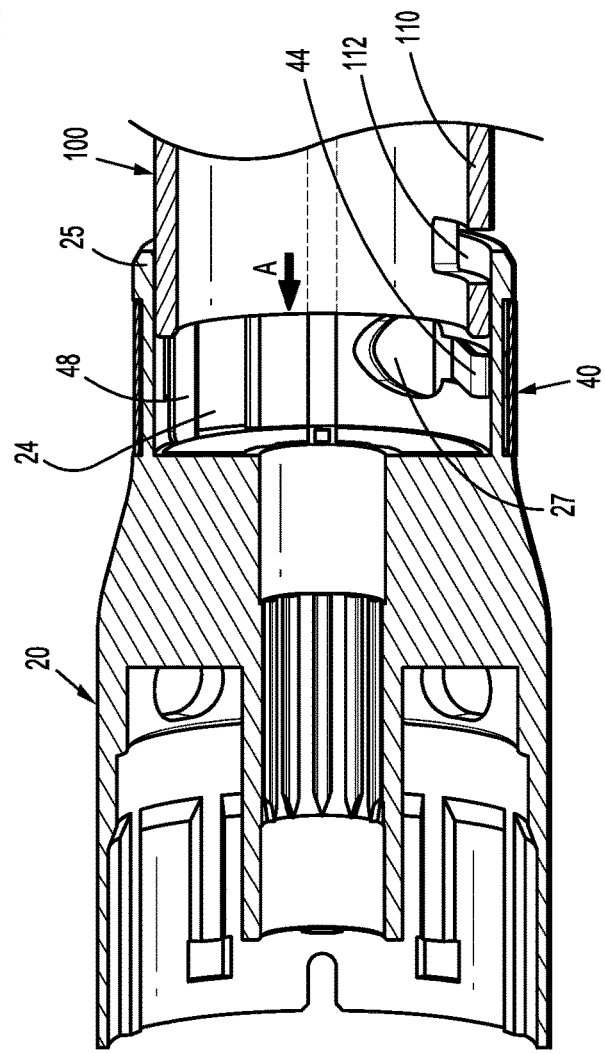
FIG. 10 is a side cross-sectional view of the loading unit and adapter of FIG. 9 with the distal end of the surgical instrument received in the proximal end of the loading unit.

With the key 29 aligned with the keyway 119, the distal end 110 of the adapter 100 is positioned within the opening 24 of the shell assembly 20 (FIG. 10). The adapter 100 is slid into the opening 24 of the shell assembly 20 until the distal end 110 of the adapter 100 is positioned adjacent the lock 44 of the retention band 40 that extends through the engagement window 27 of the shell assembly 20. The distal end 110 of the adapter 100 may be inserted into the cylindrical opening 24 until the distal end 110 abuts the lock 44 of the retention band 40 (FIG. 10).

With reference to FIG. 11, when the distal end 110 of the adapter 100 is adjacent or abutting the lock 44 of the retention band 40, the first end 42 of the retention band 40 is manually lifted in the direction indicated by Arrow B to move the first end 42 of the retention band 40 off the annular surface 23 of the shell assembly 20. When the first end 42 of the retention band 40 is lifted off the annular surface 23, the lock 44 is moved from within the engagement window 27 to permit the distal end 110 of the adapter 100 to slide into the shell assembly 20 to a position in which the attachment window 112 of the adapter 100 is longitudinally aligned with the engagement window 27 of the shell assembly 20 (FIG. 12). With the windows 27 and 112 aligned with each other, the first end 42 of the retention band 40 is released such that the retention band 40, which is in tension, clamps back onto the proximal end portion 22 of the shell assembly 20 such that the lock 44 extends through the engagement window 27 of the shell assembly 20 and the attachment window 112 of the adapter 100 to longitudinally fix the shell assembly 20 to the adapter 110. It will be appreciated that the resilience of the body 45 of the retention band 40 urges the lock 44 of the first end 42 through the windows 27 and 112 as represented by Arrow C (FIG. 12). When the lock 44 extends through the windows 27 and 112, the loading unit 10 is secured to the adapter 100.

With the loading unit secured to the adapter 100, the adapter 100 and loading unit 10 may be used to perform a surgical procedure. After surgical procedure is completed, the loading unit 10 is released from the adapter 100 by lifting the first end 42 to remove the lock 44 from the attachment window 112 of the adapter 100 and separating the loading unit 10 from the adapter 100. When the attachment window 112 is positioned distal to the engagement window 27 of the loading unit 10, the first end 42 may be released. With the loading unit 10 separated from the adapter 100, the adapter 100 may be sterilized for reuse in another surgical procedure or attached to a new loading unit for use again in the ongoing surgical procedure. In addition, the loading unit 10 may be sterilized for use in another surgical procedure or may be discarded.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method of securing a loading unit including a staple cartridge to a surgical instrument, the method comprising:
    inserting a distal end of the surgical instrument into a proximal end portion of the loading unit including the staple cartridge;
    deforming a retention band disposed on the proximal end portion of the loading unit to allow the loading unit to fully receive the distal end of the surgical instrument, the retention band having first and second ends; and
    releasing the retention band when the distal end of the surgical instrument is fully received within the proximal end portion of the loading unit to secure the loading unit to the surgical instrument.

2. The method of claim 1, further comprising attaching the retention band to the proximal end portion of the loading unit.

3. The method of claim 2, wherein attaching the retention band to the proximal end portion of the loading unit precedes inserting a distal end of the surgical instrument into the proximal end portion of the loading unit.

4. The method of claim 2, wherein attaching the retention band to the proximal end portion of the loading unit includes:
    securing the second end of the retention band to the proximal end portion of the loading unit; and
    positioning a body of the retention band within an annular groove defined in the proximal end portion of the loading unit, the body of the retention band being positioned between the first and second ends of the retention band.

5. The method of claim 4, wherein securing the second end of the retention band to the proximal end portion of the loading unit includes capturing a portion of the proximal end portion between a clip extending from the second end of the retention band and the body of the retention band.

6. The method of claim 5, wherein capturing the portion of the proximal end portion includes rotating the retention band in a first direction until a tab adjacent the second end of the retention band is disposed within a tab opening defined in the proximal end portion, the tab engaging the tab opening to prevent the retention band from rotating in a second direction opposite the first direction.

7. The method of claim 6, wherein positioning the body of the retention band within the annular groove includes positioning a lock of the retention band through an engagement window formed in the proximal end portion of the loading unit after positioning the body.

8. The method of claim 7, wherein positioning the lock of the retention band through the engagement window includes a radiating portion of the lock engaging an end surface of the engagement window spaced apart from the first end of the retention band to prevent the retention band from rotating in the second direction.

9. The method of claim 1, further comprising separating the loading unit from the surgical instrument after releasing the first end of the retention tab including:
    deforming the first end of the retention band to permit the distal end of the surgical instrument to release the proximal end portion of loading unit; and
    withdrawing the distal end of the surgical instrument from within the proximal end portion of the loading unit.

10. The method of claim 1, wherein inserting the distal end of the surgical instrument into the proximal end portion of the loading unit includes the distal end abutting a lock of the retention band extending through an engagement window of the proximal end portion, wherein deforming the first end of the retention band includes removing the lock from the engagement window, and wherein releasing the first end of the retention band when the distal end of the surgical instrument is fully received within the proximal end portion of the loading unit includes the lock of the retention band extending through the engagement window formed in the proximal end portion and an attachment window formed in the distal end of the surgical instrument to secure the loading unit to the surgical instrument.

11. A method of securing a loading unit including a staple cartridge to a surgical instrument, the method comprising:
    inserting a distal portion of the surgical instrument into a proximal end portion of the loading unit including the staple cartridge;
    deforming a retention band disposed on the proximal end portion of the loading unit such that a resilient lock of the retention band is withdrawn from an engagement window defined in the proximal end portion of the loading unit to allow the loading unit to fully receive the distal portion of the surgical instrument, the retention band secured to the loading unit by a clip extending through a clip opening defined through the proximal end portion, the resilient lock disposed adjacent a first end of the retention band; and releasing the retention band when the distal portion of the surgical instrument is fully received within the proximal end portion of the loading unit such that the resilient lock extends through an attachment window defined through the distal portion of the surgical instrument to secure the loading unit to the surgical instrument.

12. The method of claim 11, further comprising attaching the retention band to the proximal end portion of the loading unit.

13. The method of claim 12, wherein attaching the retention band to the proximal end portion of the loading unit precedes inserting the distal portion of the surgical instrument into the proximal end portion of the loading unit.

14. The method of claim 12, wherein attaching the retention band to the proximal end portion of the loading unit includes:

securing a second end of the retention band to the proximal end portion of the loading unit; and positioning a body of the retention band within an annular groove defined in the proximal end portion of the loading unit, the body of the retention band being positioned between the first and second ends of the retention band.

15. The method of claim 14, wherein securing the second end of the retention band to the proximal end portion of the loading unit includes capturing a portion of the proximal end portion between a clip extending from the second end of the retention band and the body of the retention band.

16. The method of claim 15, wherein capturing the portion of the proximal end portion includes rotating the retention band in a first direction until a tab adjacent the second end of the retention band is disposed within a tab opening defined in the proximal end portion, the tab engaging the tab opening to prevent the retention band from rotating in a second direction opposite the first direction.

17. The method of claim 16, wherein positioning the body of the retention band within the annular groove includes positioning the resilient lock of the retention band through the engagement window formed in the proximal end portion of the loading unit after positioning the body.

18. The method of claim 17, wherein positioning the resilient lock of the retention band through the engagement window includes engaging an end surface defining the engagement window spaced apart from the first end of the retention band with a radiating portion of the resilient lock to prevent the retention band from rotating in the second direction.

19. The method of claim 11, further comprising separating the loading unit from the surgical instrument after releasing the first end of the retention tab including:

deforming the first end of the retention band to permit the distal end of the surgical instrument to release the proximal end portion of loading unit; and withdrawing the distal portion of the surgical instrument from within the proximal end portion of the loading unit.

20. The method of claim 11, wherein inserting the distal portion of the surgical instrument into the proximal end portion of the loading unit includes abutting a lock of the retention band extending through an engagement window of the proximal end portion with the distal portion, wherein deforming the first end of the retention band includes removing the lock from the engagement window, and wherein releasing the first end of the retention band when the distal portion of the surgical instrument is fully received within the proximal end portion of the loading unit includes extending the lock of the retention band through the engagement window formed in the proximal end portion and an attachment window formed in the distal portion of the surgical instrument to secure the loading unit to the surgical instrument.

* * * * *